(12) United States Patent
Kawahara et al.

(10) Patent No.: US 8,481,727 B2
(45) Date of Patent: Jul. 9, 2013

(54) CRYSTALS OF HYDROCHLORIDE OF PYRIDAZIN-3(2H)-ONE COMPOUND AND PROCESS FOR PRODUCTION OF SAME

(75) Inventors: Shiro Kawahara, Funabashi (JP); Junichi Nishitani, Funabashi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 59 days.

(21) Appl. No.: 13/142,114

(22) PCT Filed: Dec. 22, 2009

(86) PCT No.: PCT/JP2009/071340
§ 371 (c)(1),
(2), (4) Date: Jun. 24, 2011

(87) PCT Pub. No.: WO2010/074090
PCT Pub. Date: Jul. 1, 2010

(65) Prior Publication Data
US 2011/0257394 A1 Oct. 20, 2011

(30) Foreign Application Priority Data

Dec. 25, 2008 (JP) .................. 2008-329799
Dec. 25, 2008 (JP) .................. 2008-330253

(51) Int. Cl.
*C07D 401/12* (2006.01)
(52) U.S. Cl.
USPC ....................................... 544/238
(58) Field of Classification Search
USPC ............................... 544/240, 238
See application file for complete search history.

(56) References Cited

U.S. PATENT DOCUMENTS

| 5,202,323 A | 4/1993 | Tanikawa et al. |
| 5,314,883 A | 5/1994 | Tanikawa et al. |
| 5,318,968 A | 6/1994 | Tanikawa et al. |

FOREIGN PATENT DOCUMENTS

| EP | 0 482 208 A1 | 4/1992 |
| EP | 0 860 169 | 8/1998 |
| WO | 91 16314 | 10/1991 |

OTHER PUBLICATIONS

Extended European Search Report issued May 29, 2012, in European Patent Application No. 09834891.5.

Mino R. Caira, "Crystalline Polymorphism of Organic Compounds", Topics in Current Chemistry, vol. 198, XP-001156954, Jan. 1, 1998, pp. 163-208.
Matsuda, Yoshihisa. "Takei Gensho o Shimesu Iyakuhin no Seizaika ni Okeru Sokudoronteki Anteisei Hyoka Ondo—Shitsudo Oyobi Hikari no Eikyo o Chushin to shite." Pharmacia, vol. 43, No. 2. pp. 111-116 (2007).
Takada, Norisachi. "Soyaku Dankai ni Okeru Gen'yaku Form Screening to Sentaku." Pharm Stage, vol. 6, No. 10. pp. 20-25 (2007).
Yamano, Mitsuhisa. "Iyakuhin no Process Kenkyu ni Okeru Kessho Takei Gensho eno Torikumi." Journal of Synthetic Organic Chemistry, vol. 65, No. 9. pp. 907(69) to 913(75) (2007).
Hata, Takehisa. "ANDAs (Kan'yaku Shin'yaku Shinsei): Iyakuhin no Kessho Takei." Pharm Stage, vol. 8, No. 6. pp. 62-69 (2008).
Iyakuhin no Zanryu Yobai Guideline ni Tsuite, Iyakushin No. 307 (1998).
Yamano, Mitsuhisa. Pharmacia, vol. 45, No. 4. p. 327 (2009).
International Search Report issued Jan. 26, 2010 in PCT/JP09/71340 filed Dec. 22, 2009.

*Primary Examiner* — Susanna Moore
*Assistant Examiner* — Cecilia M Jaisle
(74) *Attorney, Agent, or Firm* — Oblon, Spivak, McClelland, Maier & Neustadt, L.L.P.

(57) ABSTRACT

Provided are novel crystals of 4-bromo-6-(3-(4-chloro-phenyl)propoxy)-5-(pyridin-3-ylmethylamino)pyridazin-3(2H)-one monohydrochloride, and a process for production of same. A-form crystals of 4-bromo-6-(3-(4-chlorophenyl)propoxy)-5-(pyridin-3-ylmethylamino)pyridazin-3(2H)-one monohydro-chloride represented by formula (1), which exhibit a powder X-ray diffraction pattern with characteristic peaks at diffraction angles (2θ) of 8.24, 11.24, 11.76, 16.48, 17.16, 17.80, 18.24, 19.80, 21.64, 22.56, 22.96, 23.68, 24.52, 25.92, 26.32, 27.12, 27.40, 28.00, 28.64, 29.28, 31.84 and 34.80°.

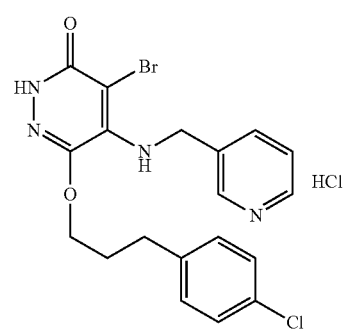

(1)

20 Claims, 2 Drawing Sheets

CRYSTALS OF HYDROCHLORIDE OF PYRIDAZIN-3(2H)-ONE COMPOUND AND PROCESS FOR PRODUCTION OF SAME

TECHNICAL FIELD

The present invention relates to crystals of 4-bromo-6-(3-(4-chlorophenyl)propoxy)-5-(pyridin-3-ylmethylamino)pyridazin-3(2H)-one mono-hydrochloride, and processes for their production.

BACKGROUND ART

4-Bromo-6-(3-(4-chlorophenyl)propoxy)-5-(pyridin-3-ylmethylamino)pyridazin-3(2H)-one mono-hydrochloride represented by the formula (1):

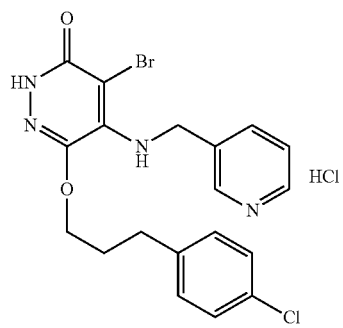

(1)

(hereinafter referred to as the compound (I)) is known to show antiplatelet properties and thus expected to be useful as a pharmaceutical product (e.g. Patent Document 1).

On the other hand, it is known that with respect to crystals of organic compounds or their salts, there usually exist crystal polymorphs having different solid structures. Further, it is known that at the time of crystallizing compounds, a solvent or water used for the crystallization is likely to be taken in to form solvate crystals (solvates) or hydrate crystals (hydrates). In this specification, such crystal polymorphs as well as solvate crystals and hydrate crystals will be generally referred to as crystal forms. These crystal forms are usually different from one another in the solubilities, dissolution rates, stabilities, hygroscopicities, melting points, handling properties, etc., and in order to develop a certain crystal of a compound as a pharmaceutical product, it is necessary to consider such characteristics comprehensively and to select a crystal form suitable for the development (e.g. Non-Patent Document 1).

However, with respect to the compound (I), Patent Document 1 discloses only that its melting point is from 188° C. to 205° C., and it discloses nothing about the crystal-form of the compound. Accordingly, in order to develop the compound (I) as a pharmaceutical product, it was necessary to find out the presence of a crystal form of this compound.

Further, in the production of a pharmaceutical product, it is necessary to obtain crystals having the same quality and the same crystal form consistently so that a constant activity and effect can be expected, and, in addition, as its industrial production method, a method is desired wherein a safety aspect is duly taken into consideration for its practical operation. With respect to the compound (I), it is known that the compound can be produced by reacting the corresponding free form with a hydrochloric acid methanol solution in a diethyl ether solvent to form a hydrochloride (e.g. Patent Document 1).

However, there is no disclosure with respect to what kind of crystal form can be obtained by this production method, and further, as an industrial production method, this method has problems such that the hydrogen chloride methanol solution is unstable, and diethyl ether is used which is a special inflammable material belonging to Class 4 of Dangerous Goods. Thus, it was necessary to find out a novel crystal form with respect to the compound (1) and at the same time to establish an industrial production method whereby such a crystal form can selectively be produced.

PRIOR ART DOCUMENTS

Patent Document

Patent Document 1: WO91/16314

Non-Patent Document

Non-Patent Document 1: Pharmacia, vol. 45, no. 4, p. 327, 2009

DISCLOSURE OF INVENTION

Technical Problem

It is an object of the present invention to find out novel crystal forms which 4-bromo-6-(3-(4-chlorophenyl)propoxy)-5-(pyridin-3-ylmethylamino)pyridazin-3(2H)-one mono-hydrochloride may take and to provide industrial processes, whereby hydrochlorides having such crystal forms can be produced consistently with the same quality in the same crystal forms and safely.

Solution to Problem

The present inventors have conducted an extensive study and as a result, have found that 4-bromo-6-(3-(4-chlorophenyl)propoxy)-5-(pyridin-3-ylmethylamino)pyridazin-3(2H)-one mono-hydrochloride may take novel crystal forms which are referred to as A-form crystal, B-form crystal and H-form crystal in this specification and have found processes for producing such crystal forms, and thus, they have accomplished the present invention.

The present invention has been made based on the above findings and provides the following.

(I):

A-form crystal of 4-bromo-6-(3-(4-chlorophenyl)propoxy)-5-(pyridin-3-ylmethylamino)pyridazin-3(2H)-one mono-hydrochloride represented by the following formula (1), which has characteristic peaks at diffraction angles (2θ) of 8.24, 11.24, 11.76, 16.48, 17.16, 17.80, 18.24, 19.80, 21.64, 22.56, 22.96, 23.68, 24.52, 25.92, 26.32, 27.12, 27.40, 28.00, 28.64, 29.28, 31.84 and 34.80° in its powder X-ray diffraction pattern:

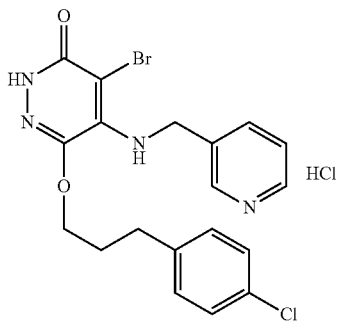

(1)

(II):

B-form crystal of 4-bromo-6-(3-(4-chlorophenyl)propoxy)-5-(pyridin-3-ylmethylamino)pyridazin-3(2H)-one mono-hydrochloride represented by the formula (1) (the same as in the above (I)), which has characteristic peaks at diffraction angles (2θ) of 11.28, 13.28, 15.84, 16.96, 19.32, 20.60, 21.32, 23.00, 24.16, 25.96, 27.72, 28.64 and 31.12° in its powder X-ray diffraction pattern.

(III):

H-form crystal of 4-bromo-6-(3-(4-chlorophenyl)propoxy)-5-(pyridin-3-ylmethylamino)pyridazin-3(2H)-one mono-hydrochloride represented by the formula (1) (the same as in the above (I)), which has characteristic peaks at diffraction angles (2θ) of 10.76, 11.32, 13.16, 16.16, 17.08, 18.76, 19.36, 23.00, 24.32, 26.00, 27.76 and 28.68° in its powder X-ray diffraction pattern.

(IV):

A process for producing A-form crystal of 4-bromo-6-(3-(4-chlorophenyl)propoxy)-5-(pyridin-3-ylmethylamino)pyridazin-3(2H)-one mono-hydrochloride as disclosed in the above (I), which comprises crystallizing 4-bromo-6-(3-(4-chlorophenyl)propoxy)-5-(pyridin-3-ylmethylamino)pyridazin-3(2H)-one represented by the following formula (2) in an alcoholic solvent or water-containing alcoholic solvent by an addition of hydrochloric acid:

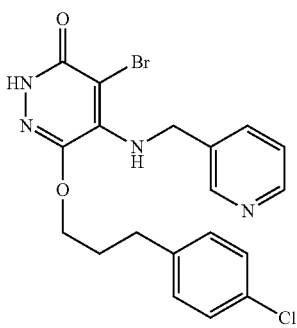

(2)

(V):

The process according to the above (IV), wherein the alcoholic solvent or water-containing alcoholic solvent is ethanol or water-containing ethanol.

(VI):

A process for producing B-form crystal of 4-bromo-6-(3-(4-chlorophenyl)propoxy)-5-(pyridin-3-ylmethylamino)pyridazin-3(2H)-one mono-hydrochloride as disclosed in the above (II), which comprises heating and dissolving 4-bromo-6-(3-(4-chlorophenyl)propoxy)-5-(pyridin-3-ylmethylamino)pyridazin-3(2H)-one represented by the formula (2) (the same as in the above (IV)) in a water-containing alcoholic solvent in the presence of hydrochloric acid, followed by quenching.

(VII):

The process according to the above (VI), wherein the water-containing alcoholic solvent is water-containing ethanol.

(VIII):

The process according to the above (VI) or (VII), wherein the compound of the formula (2) is heated and dissolved in the water-containing alcoholic solvent at a temperature of from 60° C. to 70° C., followed by quenching to a temperature of not higher than 0° C.

(IX):

A process for producing H-form crystal of 4-bromo-6-(3-(4-chlorophenyl)propoxy)-5-(pyridin-3-ylmethylamino)pyridazin-3(2H)-one mono-hydrochloride as disclosed in the above (III), which comprises heating and dissolving 4-bromo-6-(3-(4-chlorophenyl)propoxy)-5-(pyridin-3-ylmethylamino)pyridazin-3(2H)-one mono-hydrochloride represented by the formula (1) (the same as in the above (I)) in a water-containing alcoholic solvent in the presence of hydrochloric acid, and dropping the solution into an aryl alkyl ether solvent cooled to a temperature of at most 5° C. for crystallization.

(X):

The process according to the above (IX), wherein the aryl alkyl ether solvent is phenyl methyl ether.

Advantageous Effects of Invention

By the present invention, 4-bromo-6-(3-(4-chlorophenyl)propoxy)-5-(pyridin-3-ylmethylamino)pyridazin-3(2H)-one mono-hydrochlorides having novel crystal forms which are referred to as A-form, B-form and H-form, are provided, which are useful as pharmaceutical products.

Further, by the present invention, novel processes are provided, whereby the hydrochlorides having such crystal forms can be obtained consistently with the same quality and safely.

DESCRIPTION OF EMBODIMENTS

Figure 1:
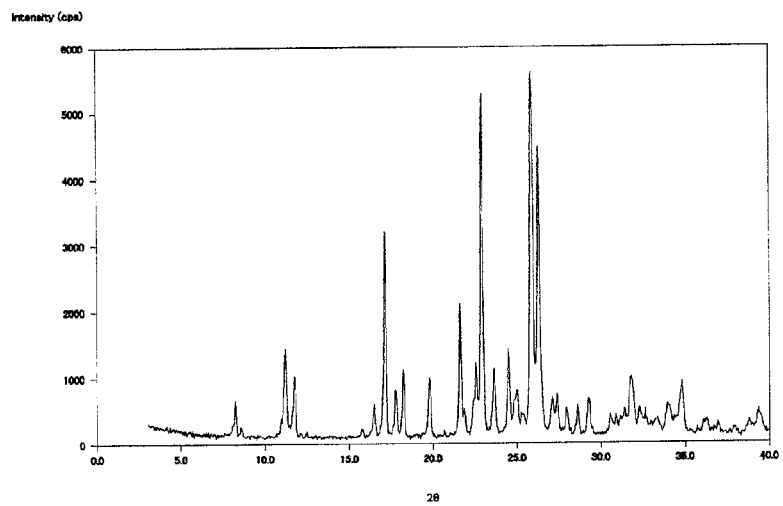
FIG. 1 shows a powder X-ray diffraction pattern of A-form crystal of 4-bromo-6-(3-(4-chlorophenyl)propoxy)-5-(pyridin-3-ylmethylamino)pyridazin-3(2H)-one mono-hydrochloride of the present invention.
Figure 2:
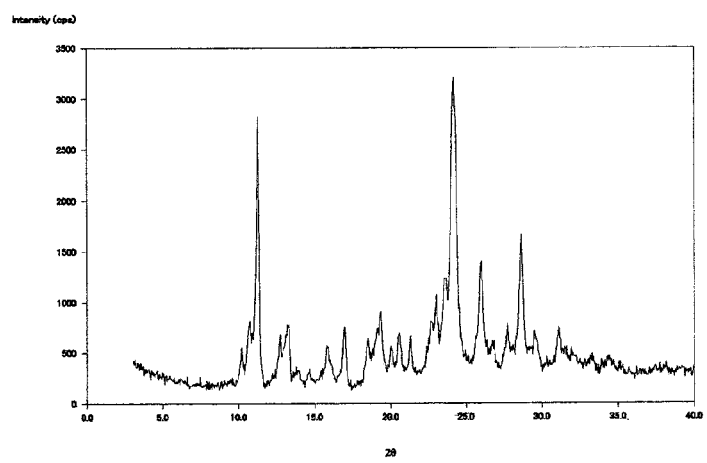
FIG. 2 shows a powder X-ray diffraction pattern of B-form crystal of 4-bromo-6-(3-(4-chlorophenyl)propoxy)-5-(pyridin-3-ylmethylamino)pyridazin-3(2H)-one mono-hydrochloride of the present invention.

In the present invention, crystal of 4-bromo-6-(3-(4-chlorophenyl)propoxy)-5-(pyridin-3-ylmethylamino)pyridazin-3(2H)-one mono-hydrochloride represented by the following formula (1), which has characteristic peaks at diffraction angles (2θ) of 8.24, 11.24, 11.76, 16.48, 17.16, 17.80, 18.24, 19.80, 21.64, 22.56, 22.96, 23.68, 24.52, 25.92, 26.32, 27.12, 27.40, 28.00, 28.64, 29.28, 31.84 and 34.80° in its powder X-ray diffraction pattern:

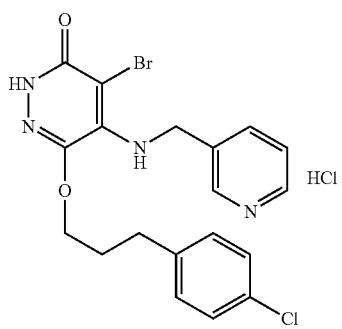

(1)

is referred to as "A-form crystal".

Further, crystal of 4-bromo-6-(3-(4-chlorophenyl)propoxy)-5-(pyridin-3-ylmethylamino)pyridazin-3(2H)-one mono-hydrochloride represented by the above formula (1), which has characteristic peaks at diffraction angles (2θ) of 11.28, 13.28, 15.84, 16.96, 19.32, 20.60, 21.32, 23.00, 24.16, 25.96, 27.72, 28.64 and 31.12° in its powder X-ray diffraction pattern, is referred to as "B-form crystal".

Further, crystal of 4-bromo-6-(3-(4-chlorophenyl)propoxy)-5-(pyridin-3-ylmethylamino)pyridazin-3(2H)-one mono-hydrochloride represented by the above formula (1), which has characteristic peaks at diffraction angles (2θ) of 10.76, 11.32, 13.16, 16.16, 17.08, 18.76, 19.36, 23.00, 24.32, 26.00, 27.76 and 28.68° in its powder X-ray diffraction pattern, is referred to as "H-form crystal".

Firstly, the process for producing A-form crystal of 4-bromo-6-(3-(4-chlorophenyl)propoxy)-5-(pyridin-3-ylmethylamino)pyridazin-3(2H)-one mono-hydrochloride, will be described.

A-form crystal can be produced by crystallizing 4-bromo-6-(3-(4-chlorophenyl)propoxy)-5-(pyridin-3-ylmethylamino)pyridazin-3(2H)-one in an alcoholic solvent or water-containing alcoholic solvent by an addition of hydrochloric acid.

The concentration of hydrochloric acid used at the time of obtaining A-form crystal is preferably from 0.5 mass % to 35 mass %, more preferably 35 mass %. The molar amount of hydrochloric acid per 1 mol of 4-bromo-6-(3-(4-chlorophenyl)propoxy)-5-(pyridin-3-ylmethylamino)pyridazin-3(2H)-one is preferably from 0.5 to 3.0 mol, more preferably from 1.0 to 2.0 mol, further preferably from 1.4 to 1.6 mol.

The entire amount of hydrochloric acid may be added all at once, or may be dividedly added.

The alcoholic solvent to be used is preferably a $C_{1-4}$ alcohol such as methanol, ethanol, 1-propanol, isopropyl alcohol, t-butyl alcohol, 1-butanol, 2-butanol, 2-ethoxyethanol, 2-methoxyethanol or trifluoroethanol, more preferably methanol, ethanol or isopropyl alcohol, further preferably ethanol.

In a case where a water-containing alcoholic solvent is used as the solvent, its water content is, having also water in hydrochloric acid taken into consideration, from 10 mass % to 80 mass %, preferably from 20 mass % to 60 mass %, more preferably from 30 mass % to 50 mass %, further preferably from 35 mass % to 40 mass %.

The amount of the water-containing alcoholic solvent to be used is preferably from 5 g to 30 g, more preferably from 10 g to 25 g, further preferably from 15 g to 20 g, per 1 g of 4-bromo-6-(3-(4-chlorophenyl)propoxy)-5-(pyridin-3-ylmethylamino)pyridazin-3(2H)-one.

As the crystallization temperature for 4-bromo-6-(3-(4-chlorophenyl)propoxy)-5-(pyridin-3-ylmethylamino)pyridazin-3(2H)-one mono-hydrochloride, a constant temperature of from 0° C. to the refluxing temperature of the solvent may be practically possible. However, preferably, a method may be mentioned wherein 4-bromo-6-(3-(4-chlorophenyl)propoxy)-5-(pyridin-3-ylmethylamino)pyridazin-3(2H)-one is heated and dissolved at a temperature of from 70° C. to 75° C. in a water-containing alcoholic solvent in the presence of hydrochloric acid, and hydrochloric acid is added, followed by cooling to at most 5° C. for precipitation of crystals.

The time for cooling is not particularly limited so long as it is at least 30 seconds, but it is usually from 5 minutes to 24 hours, preferably from 10 minutes to 10 hours. From the viewpoint of industrial production, it is preferably from 1 hour to 5 hours.

Further, at the time of crystallization, seed crystals may be used. Seed crystals may be preliminarily obtained by a method well known to those skilled in the art, such as a method of rubbing with a spatula a wall of a container containing a solution for crystallization.

Next, the process for producing B-form crystal of 4-bromo-6-(3-(4-chlorophenyl)propoxy)-5-(pyridin-3-ylmethylamino)pyridazin-3(2H)-one mono-hydrochloride will be described.

B-form crystal can be produced by heating and dissolving 4-bromo-6-(3-(4-chlorophenyl)propoxy)-5-(pyridin-3-ylmethylamino)pyridazin-3(2H)-one in a water-containing alcoholic solvent in the presence of hydrochloric acid, followed by quenching.

The concentration of hydrochloric acid used at the time of obtaining B-form crystal is preferably from 0.5 mass % to 35 mass %, more preferably from 30 mass % to 35 mass %. The molar amount of hydrochloric acid to be used is preferably from 0.5 mol to 3.0 mol, more preferably from 0.8 mol to 2.0 mol, further preferably from 1.2 mol to 1.8 mol, per 1 mol of 4-bromo-6-(3-(4-chlorophenyl)propoxy)-5-(pyridin-3-ylmethylamino)pyridazin-3(2H)-one.

The entire amount of hydrochloric acid may be added all at once, or may be dividedly added.

The alcohol in the water-containing alcoholic solvent is preferably a $C_{1-4}$ alcohol such as methanol, ethanol, isopropyl alcohol or t-butyl alcohol, more preferably methanol, ethanol or isopropyl alcohol, further preferably ethanol.

The water content of the water-containing alcohol to be used is, having also water in hydrochloric acid taken into consideration, preferably from 10 mass % to 80 mass %, more preferably from 30 mass % to 70 mass %, further preferably from 50 mass % to 60 mass %.

The amount of the water-containing alcohol to be used is preferably from 5 g of 30 g, more preferably from 10 g to 25 g, further preferably from 15 g to 20 g, per 1 g of 4-bromo-6-(3-(4-chlorophenyl)propoxy)-5-(pyridin-3-ylmethylamino)pyridazin-3(2H)-one.

As the crystallization temperature for B-form crystal, a constant temperature from 0° C. to the refluxing temperature of the solvent may practically be possible. Preferably, a method may be mentioned wherein 4-bromo-6-(3-(4-chlorophenyl)propoxy)-5-(pyridin-3-ylmethylamino)pyridazin-3(2H)-one is dissolved in ethanol or water-containing ethanol at a temperature of from 70° C. to 75° C. in the presence of hydrochloric acid, followed by quenching to not higher than 0° C. for precipitation of crystals. Here, quenching means cooling within 30 seconds, preferably within 15 seconds.

Further, seed crystals may be used at the time of crystallization. Seed crystals may preliminarily be obtained by a method well known to those skilled in the art such as a method of rubbing with a spatula a wall of a container containing a solution for crystallization.

Further, the process for producing H-form crystal of 4-bromo-6-(3-(4-chlorophenyl)propoxy)-5-(pyridin-3-ylmethylamino)pyridazin-3(2H)-one mono-hydrochloride will be described.

H-form crystal can be produced by heating and dissolving 4-bromo-6-(3-(4-chlorophenyl)propoxy)-5-(pyridin-3-ylmethylamino)pyridazin-3(2H)-one mono-hydrochloride in a water-containing alcoholic solvent in the presence of hydrochloric acid, and dropping the solution into an aryl alkyl ether solvent cooled to a temperature of at most 5° C. for crystallization.

H-form crystal of 4-bromo-6-(3-(4-chlorophenyl)propoxy)-5-(pyridin-3-ylmethylamino)pyridazin-3(2H)-one mono-hydrochloride may be obtained from A-form crystal of the same, but a small excess of hydrochloric acid is required to coexist. That is, hydrochloric acid having a concentration of 35 mass % is used in an amount of preferably from 0.1 mol to 2.0 mol, more preferably from 0.2 mol to 1.0 mol, further preferably from 0.3 mol to 0.7 mol, per 1 mol of 4-bromo-6-(3-(4-chlorophenyl)propoxy)-5-(pyridin-3-ylmethylamino)pyridazin-3(2H)-one mono-hydrochloride.

The entire amount of hydrochloric acid may be added all at once, or may be dividedly added.

The alcohol for the water-containing alcoholic solvent is preferably a $C_{1-4}$ alcohol such as methanol, ethanol, isopropyl alcohol or t-butyl alcohol, more preferably methanol, ethanol or isopropyl alcohol, further preferably ethanol. The water content in the water-containing alcohol is, having also water in hydrochloric acid taken into consideration, preferably from 10 mass % to 80 mass %, more preferably from 30 mass % to 70 mass %, further preferably from 50 mass % to 60 mass %.

The amount of the water-containing alcoholic solvent to be used is preferably from 5 g to 30 g, more preferably from 10 g to 25 g, further preferably from 12 g to 18 g, per 1 g of 4-bromo-6-(3-(4-chlorophenyl)propoxy)-5-(pyridin-3-ylmethylamino)pyridazin-3(2H)-one mono-hydrochloride.

H-form crystal can be precipitated by dissolving the hydrochloride in the heated water-containing alcoholic solvent in the presence of hydrochloric acid and dropping the solution into the aryl alkyl ether cooled to a temperature of at most 5° C. This aryl alkyl ether is phenyl methyl ether or phenyl ethyl ether, and particularly from the viewpoint of common applicability, phenyl methyl ether (another name: anisole) is preferred.

The amount of phenyl methyl ether to be used is preferably from 10 g to 100 g, more preferably from 30 g to 70 g, further preferably from 50 g to 60 g, per 1 g of 4-bromo-6-(3-(4-chlorophenyl)propoxy)-5-(pyridin-3-ylmethylamino)pyridazin-3(2H)-one mono-hydrochloride.

Further, seed crystals may be used at the time of the crystallization. The seed crystals may preliminarily be obtained by a method well known to those skilled in the art such as a method of rubbing with a spatula a wall of a container containing a solution for crystallization.

In this specification, hydrochloric acid means an aqueous solution of hydrogen chloride. Instead of hydrochloric acid, an organic solvent solution of hydrogen chloride, e.g. a hydrogen chloride methanol solution or a hydrogen chloride dioxane solution may, for example, be used. However, from the viewpoint of safety, etc. in an industrial use, it is advisable to use hydrochloric acid.

When A-from crystal, B-form crystal and H-form crystal are compared from the viewpoint of industrial production, A-form crystal and B-form crystal are superior to H-form crystal in that as the solvent to be used, it is possible to select an alcohol which can be industrially readily utilized. Further, A-form crystal is superior to B-form crystal in that it does not require quenching.

EXAMPLES

Now, the present invention will be described in detail with reference to Examples, but it should be understood that the present invention is by no means limited thereto. The DSC analysis in Examples was carried out by means of DSC8230 manufactured by Rigaku Corporation by using about 5 mg of a sample and by raising the temperature at a rate of 5° C. per minute. Further, the powder X-ray diffraction measurement was carried out by means of MXLabo (Ray source: Cu·Kα, wavelength: 1.54056 ($10^{-10}$ m)) manufactured by MacScience. Further, the melting point measurement was carried out by using YANAKO MP-500V manufactured by Yanagimoto Mfg. Co., Ltd.

Here, DSC means a differential scanning calorimetry, and UV means ultraviolet ray.

As 35% hydrochloric acid disclosed in Examples, hydrochloric acid commercially available as 35 mass % was employed.

Example 1

Production of A-Form Crystal

4-Bromo-6-(3-(4-chlorophenyl)propoxy)-5-(pyridin-3-ylmethylamino)pyridazin-3(2H)-one (25.8 kg), water (168.9 kg), ethanol (132.6 kg) and 35% hydrochloric acid (6.57 kg) were mixed and heated to 70° C. This mixture was, while being hot, filtrated, then washed with a mixed liquid of water (58.8 kg), ethanol (43.9 kg) and 35% hydrochloric acid (2.36 kg) and heated to a temperature of from 70 to 75° C., whereupon dissolution was confirmed. This mixture was cooled to at most 5° C. over a period of 4 hours, and seed crystals were added on the way at 50° C. to let crystals precipitate. The temperature was maintained to be at most 5° C. for 2 hours, whereupon precipitated crystals were collected by filtration and then dried under reduced pressure at 60° C. to obtain 25.4 kg of white crystals. The melting point of the obtained crystals was from 200° C. to 215° C., and the powder X-ray diffraction pattern had characteristic peaks at diffraction angles 2θ of 8.24, 11.24, 11.76, 16.48, 17.16, 17.80, 18.24, 19.80, 21.64, 22.56, 22.96, 23.68, 24.52, 25.92, 26.32, 27.12, 27.40, 28.00, 28.64, 29.28, 31.84 and 34.80°.

Example 2

Production of B-Form Crystal

4-Bromo-6-(3-(4-chlorophenyl)propoxy)-5-(pyridin-3-ylmethylamino)pyridazin-3(2H)-one (6.00 g), water (39.27 g), ethanol (30.86 g) and 35% hydrochloric acid (1.40 g) were mixed. Further, water (13.71 g), ethanol (10.25 g) and 35% hydrochloric acid (0.71 g) were added, and the mixture was heated to a temperature of from 63° C. to 68° C. and dissolved. Liquid nitrogen was introduced thereto all at once, and the mixture was left to stand for one hour, whereupon precipitated crystals were collected by filtration and dried under reduced pressure at 40° C. to obtain 5.91 g of white crystals. As a result of the DSC analysis of the obtained crystals, a heat generation peak was observed at 139° C., and a heat absorption peak was observed at 215° C. Further, the powder X-ray diffraction pattern of the obtained crystals had characteristic peaks at diffraction angles 2θ of 11.28, 13.28, 15.84, 16.96, 19.32, 20.60, 21.32, 23.00, 24.16, 25.96, 27.72, 28.64 and 31.12°.

Example 3

Production of H-Form Crystal

4-Bromo-6-(3-(4-chlorophenyl)propoxy)-5-(pyridin-3-ylmethylamino)pyridazin-3(2H)-one mono-hydrochloride (8.44 g), water (68.84 g), ethanol (53.46 g) and 35% hydrochloric acid (0.90 g) were mixed, heated to 85° C. and dissolved. This heated solution was dropped into phenyl methyl ether (anisole) (488.68 g) cooled to at most 5° C. Precipitated crystals were collected by filtration, washed twice with 10 ml of ethanol and then dried under reduced pressure at 40° C. to obtain 6.75 g of white crystals. As a result of the DSC analysis of the obtained crystals, a heat generation peak was observed at 134° C., and a heat absorption peak was observed at 215° C. Further, the powder X-ray diffraction pattern of the obtained crystals had characteristic peaks at diffraction angles 2θ of 10.76, 11.32, 13.16, 16.16, 17.08, 18.76, 19.36, 23.00, 24.32, 26.00, 27.76 and 28.68°.

Test Example 1

Figure 3:
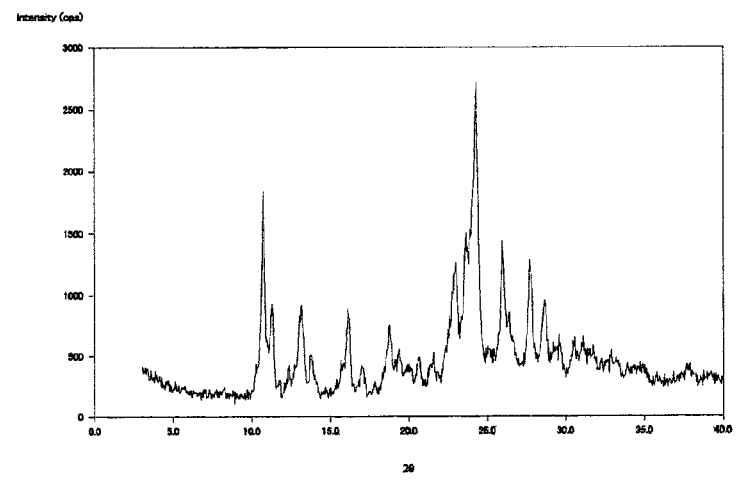
FIG. 3 shows a powder X-ray diffraction pattern of H-form crystal of 4-bromo-6-(3-(4-chlorophenyl)propoxy)-5-(pyridin-3-ylmethylamino)pyridazin-3(2H)-one mono-hydrochloride of the present invention.
Figure 4:
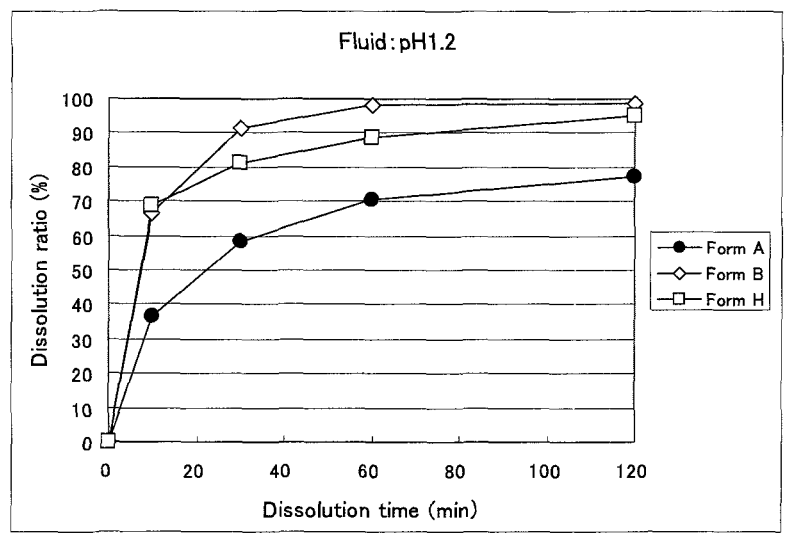
FIG. 4 shows the results of dissolution tests of A-form crystal, B-form crystal and H-form crystal in a dissolution test first fluid (pH 1.2) as measured in Test Example 1.
Figure 5:
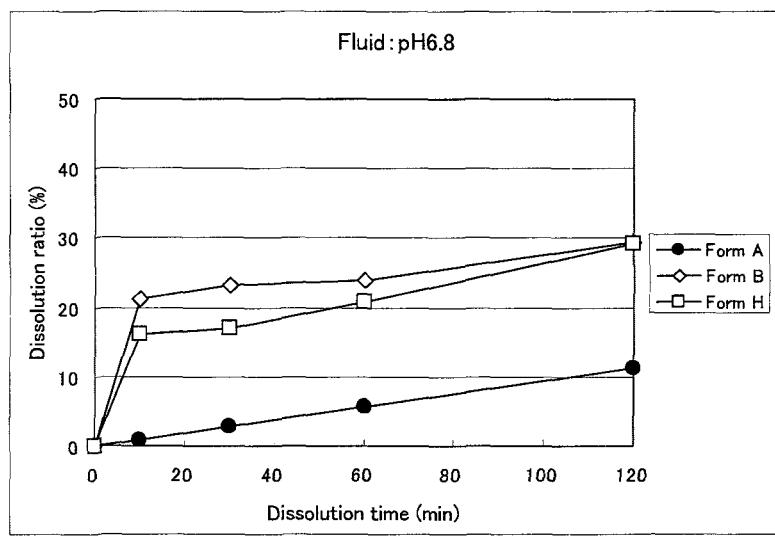
FIG. 5 shows the results of dissolution tests of A-form crystal, B-form crystal and H-form crystal in a dissolution test second fluid (pH 6.8) as measured in Test Example 1.

Dissolution test of 4-bromo-6-(3-(4-chlorophenyl) propoxy)-5-(pyridin-3-ylmethylamino)pyridazin-3 (2H)-one mono-hydrochlorides About 10 mg of each of A-form crystal (Form A) obtained in Example 1, B-form crystal (Form B) obtained in Example 2 and H-form crystal (Form H) obtained in Example 3 was sampled, and a test was carried out at 50 rpm by the dissolution test method paddle method in Japanese Pharmacopoeia using 900 ml of a test fluid. Upon expiration of 10 minutes, 30 minutes, 60 minutes and 120 minutes after initiation of the test, sampling was carried out, and UV measurements were carried out, whereupon the dissolution ratios were calculated. Here, as the dissolution tester, NTR-VS6P manufactured by TOYAMA SANGYO CO., LTD. was used; as the spectrophotometer, UV-2400PC manufactured by Shimadzu Corporation was used; and as the test fluid, the dissolution test first fluid (pH 1.2) and second fluid (pH 6.8) were used. The results are shown in FIGS. 3 and 4 (the ordinate represents the dissolution ratio (%), and the abscissa represents the dissolution time (minutes)). From FIGS. 3 and 4, B-form crystal and H-form crystal were found to be superior to A-form crystal in solubility.

INDUSTRIAL APPLICABILITY

4-Bromo-6-(3-(4-chlorophenyl)propoxy)-5-(pyridin-3-ylmethylamino)pyridazin-3(2H)-one mono-hydrochlorides having novel crystal forms referred to as A-form, B-form and H-form, according to the present invention, are useful in that they can be produced consistently with the same crystal-forms, and they can be produced safely with the same quality.

The entire disclosures of Japanese Patent Application No. 2008-329799 filed on Dec. 25, 2008 and Japanese Patent Application No. 2008-330253 filed on Dec. 25, 2008 including specifications, claims, drawings and summaries are incorporated herein by reference in their entireties.

The invention claimed is:

1. An A-form crystal of 4-bromo-6-(3-(4-chlorophenyl) propoxy)-5-(pyridin-3-ylmethylamino)pyridazin-3(2H)-one mono-hydrochloride of formula (1),

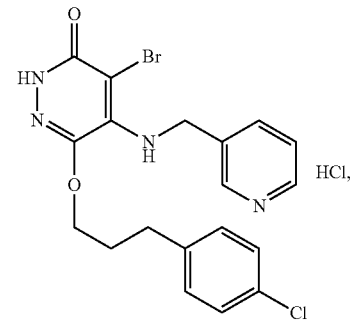

(1)

which has characteristic peaks at diffraction angles (2θ) of 8.24, 11.24, 11.76, 16.48, 17.16, 17.80, 18.24, 19.80, 21.64, 22.56, 22.96, 23.68, 24.52, 25.92, 26.32, 27.12, 27.40, 28.00, 28.64, 29.28, 31.84 and 34.80° in its powder X-ray diffraction pattern.

2. A B-form crystal of 4-bromo-6-(3-(4-chlorophenyl)propoxy)-5-(pyridin-3-ylmethylamino)pyridazin-3(2H)-one mono-hydrochloride of formula (1),

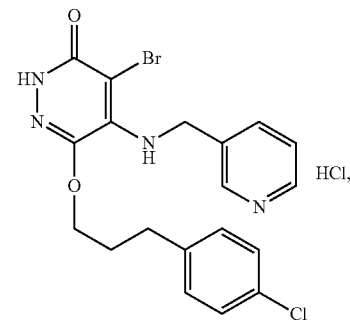

(1)

which has characteristic peaks at diffraction angles (2θ) of 11.28, 13.28, 15.84, 16.96, 19.32, 20.60, 21.32, 23.00, 24.16, 25.96, 27.72, 28.64 and 31.12° in its powder X-ray diffraction pattern.

3. An H-form crystal of 4-bromo-6-(3-(4-chlorophenyl) propoxy)-5-(pyridin-3-ylmethylamino)pyridazin-3(2H)-one mono-hydrochloride of formula (1),

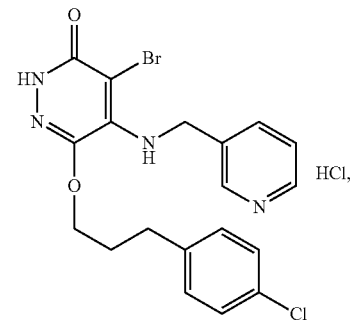

(1)

which has characteristic peaks at diffraction angles (2θ) of 10.76, 11.32, 13.16, 16.16, 17.08, 18.76, 19.36, 23.00, 24.32, 26.00, 27.76 and 28.68° in its powder X-ray diffraction pattern.

4. A process for producing the A-form crystal of claim 1, the process comprising:
  crystallizing 4-bromo-6-(3-(4-chlorophenyl)propoxy)-5-(pyridin-3-ylmethylamino)pyridazin-3(2H)-one from an alcoholic solvent or water-comprising alcoholic solvent by adding hydrochloric acid,
  wherein the 4-bromo-6-(3-(4-chlorophenyl)propoxy)-5-(pyridin-3-ylmethylamino)pyridazin-3(2H)-one is of by formula (2):

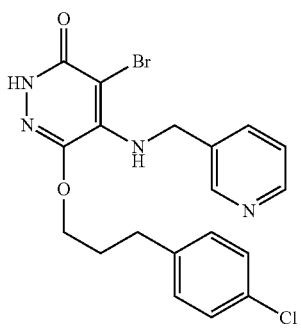

(2)

5. The process of claim 4, wherein the alcoholic solvent or water-comprising alcoholic solvent is ethanol or water-comprising ethanol.

6. A process for producing the B-form crystal of claim 2, the process comprising:
  heating and dissolving 4-bromo-6-(3-(4-chlorophenyl)propoxy)-5-(pyridin-3-ylmethylamino)pyridazin-3(2H)-one in a water-comprising alcoholic solvent in the presence of hydrochloric acid, followed by
  quenching the 4-bromo-6-(3-(4-chlorophenyl)propoxy)-5-(pyridin-3-ylmethylamino)pyridazin-3(2H)-one, thereby producing the B-form crystal,
  wherein the 4-bromo-6-(3-(4-chlorophenyl)propoxy)-5-(pyridin-3-ylmethylamino)pyridazin-3(2H)-one is of formula (2):

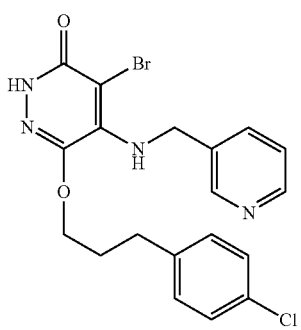

(2)

7. The process of claim 6, wherein the water-comprising alcoholic solvent is water-comprising ethanol.

8. The process of claim 6, wherein the compound of formula (2) is heated and dissolved in the water-comprising alcoholic solvent at a temperature of from 60° C. to 70° C., followed by quenching to a temperature of not higher than 0° C.

9. A process for producing the H-form crystal of claim 3, the process comprising:
  heating and dissolving 4-bromo-6-(3-(4-chlorophenyl)propoxy)-5-(pyridin-3-ylmethylamino)pyridazin-3(2H)-one mono-hydrochloride in a water-comprising alcoholic solvent in the presence of hydrochloric acid to obtain a solution; and
  dropping the solution into an aryl alkyl ether solvent cooled to a temperature of at most 5° C., thereby producing the H-form crystal,
  wherein the 4-bromo-6-(3-(4-chlorophenyl)propoxy)-5-(pyridin-3-ylmethylamino)pyridazin-3(2H)-one mono-hydrochloride is of formula (1)

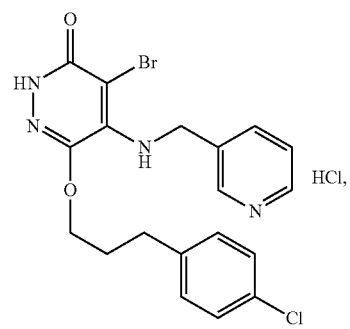

(1)

10. The process of claim 9, wherein the aryl alkyl ether solvent is phenyl methyl ether.

11. The process of claim 7, wherein the compound of formula (2) is heated and dissolved in the water-comprising alcoholic solvent at a temperature of from 60° C. to 70° C., followed by quenching to a temperature of not higher than 0° C.

12. The process of claim 4, wherein the water-comprising alcoholic solvent is present and a water content thereof, also accounting for water in the hydrochloric acid, is from 10 mass % to 80 mass %.

13. The process of claim 4, wherein the water-comprising alcoholic solvent is present and a water content thereof, also accounting for water in the hydrochloric acid, is from 20 mass % to 60 mass %.

14. The process of claim 4, wherein the water-comprising alcoholic solvent is present and a water content thereof, also accounting for water in the hydrochloric acid, is from 30 mass % to 50 mass %.

15. The process of claim 4, wherein the water-comprising alcoholic solvent is present and a water content thereof, also accounting for water in the hydrochloric acid, is from 35 mass % to 40 mass %.

16. The process of claim 4, wherein the alcoholic solvent or water-comprising alcoholic solvent is methanol or water-comprising methanol.

17. The process of claim 4, wherein the alcoholic solvent or water-comprising alcoholic solvent is isopropyl alcohol or water-comprising isopropyl alcohol.

18. The process of claim 8, wherein the quenching comprises cooling from a temperature of from 60° C. to 70° C. to a temperature of not higher than 0° C. within a cooling time of 30 seconds.

19. The process of claim 8, wherein the quenching comprises cooling from a temperature of from 60° C. to 70° C. to a temperature of not higher than 0° C. within a cooling time of 15 seconds.

20. The process of claim 4, wherein the water-comprising alcoholic solvent is present and an amount of the water-comprising alcoholic solvent is from 5 g to 30 g, per 1 g of 4-bromo-6-(3-(4-chlorophenyl)propoxy)-5-(pyridin-3-ylmethylamino)pyridazin-3(2H)-one.

* * * * *